(12) United States Patent
Shelvey

(10) Patent No.: US 6,353,077 B2
(45) Date of Patent: *Mar. 5, 2002

(54) CURABLE COMPOSITIONS

(76) Inventor: Michael Francis Shelvey, Hillcroft, Fangfoss, York, Y04 50J (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/029,971

(22) PCT Filed: Mar. 9, 1996

(86) PCT No.: PCT/GB96/02258

§ 371 Date: May 26, 1998

§ 102(e) Date: May 26, 1998

(87) PCT Pub. No.: WO97/10275

PCT Pub. Date: Mar. 20, 1997

(30) Foreign Application Priority Data

Sep. 13, 1995 (GB) .............................................. 9518749

(51) Int. Cl.⁷ .............................................. C08G 18/10
(52) U.S. Cl. ...................... 528/58; 528/59; 252/182.22; 602/8
(58) Field of Search ................ 528/58, 59; 252/182.22; 602/8

(56) References Cited

U.S. PATENT DOCUMENTS

| | | | | | |
|---|---|---|---|---|---|
| 4,427,003 A | * | 1/1984 | Fennimore | .................... | 128/90 |
| 4,705,840 A | * | 11/1987 | Buckanin | ..................... | 528/53 |
| 4,824,595 A | * | 4/1989 | Richter | .................. | 252/182.17 |
| 5,027,804 A | * | 7/1991 | Forsyth | ........................ | 128/90 |
| 5,225,513 A | * | 7/1993 | Scholz | ......................... | 528/53 |

FOREIGN PATENT DOCUMENTS

| | | | |
|---|---|---|---|
| GB | 1578895 | * | 11/1980 |
| WO | 81-00671 | * | 3/1981 |
| WO | 88-02636 | * | 4/1988 |
| WO | 94-02525 | * | 2/1994 |
| WO | 96-06873 | * | 3/1996 |

* cited by examiner

Primary Examiner—Rachel Gorr
(74) Attorney, Agent, or Firm—Adams, Schwartz & Evans, P.A.

(57) ABSTRACT

A resin system comprising at least water curable isocyanate functionalized prepolymer and a first catalyst which is chemically bound-in and a second catalyst which is not chemically bound-in. The two catalysts together show a synergistic effect, and the resin system is particularly suitable for orthopaedic splinting applications.

34 Claims, No Drawings

CURABLE COMPOSITIONS

The present invention relates to curable resin compositions and in particular to isocyariate functionalised resin systems suitable for use in medical applications, such as orthopaedic splinting.

A favoured method for curing isocyanate functionalised resins is to use water curing. Water curing can be achieved by many means, for example the resin being immersed in water, contact with atmospheric moisture or by being sprayed with water after application.

As used herein water curable means that the resin system is capable of hardening to a rigid or semi-rigid structure on exposure to water.

Any isocyanate based resin system depending on the reaction of an isocyanate functional group with water, an amine group or an alcohol group for curing may benefit from the use of catalysts to speed up the curing so that the resin sets in an acceptably short time.

The use of inorganic carbonate catalysts has been proposed with functionalised isocyanate resin systems, however the shelf life may be affected in the presence of any moisture, as the catalyst is in direct contact with the resin and would be set off in the presence of moisture. More recently alternative catalysts based on tertiary amines have been used with isocyanate functionalised resin systems in Patent Application WO88/02636, U.S. Pat. No. 5,027,804 and U.S. Pat. No. 4,427,003.

Reactive tertiary amines are rarely fully chemically incorporated into the polyurethane during the isocyanate-water reaction. In addition, such tertiary amines may be vaporised by the exotherm generated during the polyurethane reaction. Thus, there is the possibility that catalyst may leach out or evaporate from the resin system during cure or after curing. Such amines may have a strong odour and the potential inhalation and absorption toxicity of tertiary amines is well known.

Patent Application WO94/02525 partially addresses the problems encountered with tertiary amine catalysts by modifying reactive tertiary amine catalysts by mixing under reaction conditions a reactive tertiary amine, a polyol and an organic isocyanate compound to give a catalyst which has a higher molecular weight and may therefore be retained more.

Patent Application WO94/05475 discloses a tertiary amine as a polyurethane reaction catalyst, where the catalyst is added to a binder containing isocyanate groups. Lignocellulose fibres are coated with the binder and then shaped into a mat which is pressed under the influence of heat to form a board, where the catalyst is subsequently built into the board.

However such catalysts may still be prone to leaching especially when used in a water curable isocyanate composition.

It may be possible to use a lower level of catalysts to reduce the problems discussed above, however such a catalyst is unlikely to be suitable for rapid cure systems, as would be required for am orthopaedic splinting material.

The present invention seeks to overcome these disadvantages by providing a water curable isocyanate functionalised resin system with catalysts which are not a potential hazard due to leachable or volatile components.

The use of a chemically bound-in tertiary amine catalyst would overcome the problems associated with the leaching of catalyst. By "chemically bound-in" is meant a catalyst that is ionically and/or covalently bound to the curable isocyanate functionalised prepolymer.

Furthermore the use of more than one catalyst may benefit the curing speed of isocyanate functionalised resin systems.

Surprisingly it was found that the curing reaction of a water curable isocyanate functionalised resin, when catalysed by a first and a second catalyst resulted in a greatly increased curing rate of the resin as the two catalysts together showed a synergistic effect.

The synergistic effect described in this invention is the increase in the reaction rate between water and isocyanate functionalised prepolymers in polyurethane/urea synthesis.

Thus according to the present invention there is provided a resin system comprising at least a water curable, isocyanate functionalised prepolymer and a first and second catalyst component wherein the first catalyst is chemically bound-in to the prepolymer and the second catalyst is not chemically bound-in.

Chemically bound-in catalysts include catalysts bonded covalently and/or ionically to the isocyanate functionalised prepolymer.

Preferably the first chemically bound-in catalyst is covalently bound-in to the prepolymer.

Preferably the first catalyst is a tertiary amine catalyst.

Suitable tertiary amine catalysts comprise both a tertiary amine group and an isocyanate reactive group.

The term "isocyanate reactive group" refers to a group which forms a covalent bond when reacted with an isocyanate group (—NCO) under appropriate conditions, these include for example hydroxy and amine groups as well as carboxylic acids, thiols, anhydrides, urethanes, ureas and other such groups with an active hydrogen atom known to one skilled in the art.

Preferably the chemically bound-in tertiary amine catalyst is covalently bound-in to the prepolymer.

The bound-in tertiary amine catalyst may be present at any appropriate location in the isocyanate prepolymer. For example they may be introduced at an end of the isocyanate prepolymer molecules via a capping reaction, they may be present on a side chain extending from the main polymer backbone, or may be part of the polymer backbone itself.

The tertiary amine catalyst may be optionally substituted with substituents which do not substantially adversely affect the reaction of the tertiary amine catalyst with the isocyanate functionalised prepolymer or the catalytic effect of the tertiary amine catalyst when present in the isocyanate functionalised prepolymers of the resin system of the present invention.

Appropriate tertiary amine catalysts for reacting with isocyanates so as to form the prepolymers of the present invention may include but are not limited to the molecules listed below.

1-(2-Hydroxyethyl)pyrrolidine, 1-methyl piperazine,
1-methyl-2-piperidine methanol,
1,4-bis(2-hydroxyethyl)piperazine
2[2-(dimethylamino)ethyl]methyl amino ethanol,
gramine, 3-morpholino-1,2-propanediol,
1,4-bis(3-aminopropyl)piperazine, tropine,
3-aminopropyl morpholine, 4,2-hydroxyethyl morpholine,
3,3-diamino-N-methyl dipropylamine,
1,4-bis(2-hydroxypropyl)-2-methylpiperazine,
1-(2-hydroxypropyl)imidazole, 3-dimethyl amino propanol
and β-hydroxy-4-morpholine propane sulphonic acid.

The chemically bound-in tertiary amine catalysts may comprise a single species or mixture of species. Further, several species of such bound-in tertiary amines may be present within a prepolymer composition or within one isocyanate functionalised prepolymer molecule.

Any one of the prepolymer molecules may contain a single bound-in tertiary amine catalyst of a single species or more than one tertiary amine catalyst of a number of species.

In addition any one prepolymer molecule may comprise more than one tertiary amine catalyst either present on a side chain, as end groups or part of the polymer backbone, for example when the tertiary amine catalysts comprise two or more isocyanate reactive catalysts and act as chain extenders.

The isocyanates used to react with the tertiary amine catalyst comprising both a tertiary amine group and an isocyanate reactive group may be any suitable isocyanates well known in the art, for example aliphatic, cycloaliphatic, aromatic or heterocyclic isocyanates. Preferably aliphatic isocyanates are used.

Whatever species of tertiary amine containing molecules are utilised to prepare a bound-in catalyst, it is preferred that they comprise less than 10% by weight and more preferably from 0.1 to 5% by weight of the curable composition.

The second catalyst comprises preferably 0.05 to 10% and more prefereably 0.1 to 5% by weight of the curable composition. The second catalyst is preferably water soluble but insoluble in the prepolymer. The second catalyst is preferably a solid inorganic catalyst. For example the second catalyst is aptly a group I or II alkali metal salt and preferably a group I metal salt, such as a group I metal salt, for example a group Ia metal carbonate. An apt example of a group Ia metal carbonate is potassium carbonate.

Suitably the first and second catalyst together comprise less than 7.5% by weight of the resin system.

Preferably equal amounts of the first and second catalyst are added to resin system, for example 1.0%, 1.25%, 2% or 2.5% of each of the first and second catalyst by weight of the resin system may be added.

The second catalyst is dispersed in the curable prepolymer of the invention using methods known to those skilled in the art.

A problem often associated with the use of inorganic carbonate catalysts is where the shelf life of the curable resin system is reduced due to the increased reactivity of the isocyanate functionalised prepolymer with atmospheric moisture in the presence of a carbonate catalyst. This may be avoided by coating the carbonate catalyst with a coating that is insoluble in atmospheric moisture and is soluble in water, or water pervious once the coating is hydrated.

A preferred feature of the present invention, although not essential is the pre-treatment of the selected solid inorganic catalyst with a hydrophilic coating, before dispersion in the prepolymer. This reduces the risk of ageing of the resin system.

The hydrophilic coating may be any suitable coating that will dissolve on contact with water or become hydrated with water such that the hydrated coating becomes water pervious, for example polyvinyl alcohol (PVA) or polyhydroxyethylmethacrylate (poly HEMA).

Further according to the present invention there is provided a process for making a curable resin system as hereinbefore described wherein isocyanates and molecules comprising both a tertiary amine group and an isocyanate reactive group are reacted to give an isocyanate functionalised prepolymer into which is mixed a coated solid inorganic catalyst.

For a reaction based on an aromatic isocyanate functionalised resin the use of two catalysts are herein before described would allow an overall reduction in the amount of catalyst required, therefore reducing toxicological aspects and costs.

This invention is particularly suitable for the curing reaction of aliphatic isocyanate functionalised prepolymers which are well known in the art for having a much slower cure time than aromatic isocyanate functionalised prepolymers, and have therefore been considered unsuitable up until now for use in orthopaedic splinting applications.

The use of aliphatic isocyanates allows the preparation of prepolymers with a larger range of viscosities. The use of aromatic isocyanates usually results in more viscous prepolymers which may not be as suitable for orthopaedic applications. Furthermore polymers based on aliphatic isocyanates do not tend to yellow on ageing.

The use of at least two catalysts as hereinbefore described comprising in total preferably less than 10% by weight of the curable composition has made it possible to consider the use of aliphatic based isocyanates for orthopaedic splinting materials.

In a further embodiment of the present invention there is provided an orthopaedic splinting material comprising a flexible substrate carrying a resin system as hereinbefore described.

Preferred formulations according to the present invention can include effective amounts of a variety of additives conventional in the art. These additives may comprise fillers, pigments, fragrances, surfactants lubricants, or mixtures thereof. Effective amounts are amounts sufficient to provide the benefits of the additive.

Suitably powdered fillers include but are not limited to talc, calcium carbonate, fumed silica sold under the trade name CAB-O-SIL™, alumina and fibrous reinforcing fillers such as wollastonites (calcium metasilicate), to impart desirable viscosity and handling characteristics.

The fillers may be present as single chemical species or as mixtures and, when used, are aptly present in an amount of up to 50% w/w, preferably up to 20% w/w and aptly at least 1.0% w/w of the resin.

Although the splinting material of the present invention is described in terms of "an orthopaedic splinting material", the term is also intended to embrace casts, supports and braces, where such casts, splints, supports and braces do not necessarily surround the whole limb or other body portion.

The resin system used in the bandages of the invention according to the invention may be carried on any substrate suitable for a casting, splinting, bracing or support material.

The resin system employed in the invention may be coated, laminated, sprayed or impregnated onto a suitable substrate using conventional methods in the art. Aptly the splinting material of the invention is prepared by nip-coating the resin system onto the substrate.

Aptly the splinting material of the present invention may be prepared by using a substrate carrying the second catalyst and subsequently coating or impregnating the substrate with a prepolymer as hereinbefore described comprising an isocyanate functionalised prepolymer and the first catalyst which is chemically bound-in to the prepolymer.

For use as an orthopaedic splinting material, the viscosity of the resin system is preferably suitable for application to a substrate. Furthermore the viscosity is preferably such that the resin system remains in place on and within the substrate, while in storage and during curing.

Aptly the resin systems of the invention have viscosities ranging from 1,000 to 100,000 mPas$^{-1}$, and more preferably from 40,000 to 60,000 mPas$^{-1}$.

A preferred substrate is a flexible fabric carrier which may be a woven, knitted or non woven fabric which can carry enough of the resin system of the invention to ensure that the resultant splint has adequate strength. The substrate should be sufficiently porous to allow water to come into contact with the carried resin system when the splinting material is immersed in water. The substrate may be in the form of tapes, bandages, sheets or other conventional forms, apt for preparing for example orthopaedic casting bandages, splinting materials, braces or supports.

Suitable materials for forming the substrate include polyester, nylon, polypropylene, polyamides, polyolefins and glass fibre or mixtures thereof. Examples of such substrates are disclosed in Patent Nos. U.S. Pat. No. 4,427,002, U.S. Pat. No. 4,627,424 and EP 326,285.

Aptly the substrate may be a mesh having openings through it to enable the water to penetrate into the rolled bandage to contact all parts of the resin system. The openings will permit circulation of air and aid evaporation of moisture from the skin beneath the cured cast.

Preferably the mesh is of a loose weave or knit so as to allow at least partial impregnation as well as coating by the resin system.

The amount of resin carried by the substrate may vary depending on the intrinsic properties of the resin system and should be sufficient to ensure that the resultant cast has adequate strength.

Suitable amounts range from 30 to 80% w/w of the resin system which are calculated using the equation:

$$\frac{\text{weight of (substrate + resin)} - \text{weight of (substrate)}}{\text{weight (substrate + resin)}} \times 100\%$$

Preferably 40 to 70% w/w and most preferably 50 to 65% w/w of the resin system are used.

The orthopaedic splinting materials may be used to form a hardened cast by wetting and shaping the wet material around a body member or part thereof and allowing the resin system to cure.

Upon curing the resin system generally becomes bonded, physically or chemically to the substrate.

Aptly wetting is achieved by immersing the splinting material in water, and removing any excess water, for example, by squeezing the splinting material several times before application to the body member.

When removed from the water the splinting material can be readily wrapped about the limb which is to be immobilised and wherein the limb is preferably protected with a conventional underlying stockinet or padding.

Extra cushioning may be provided in the form of undercast padding.

An alternative method for forming a cast or splint comprises applying the splinting material of the invention to the body member to be immobilised followed by spraying the material with water.

The curing reaction of the resin system should be sufficiently slow to allow the splinting material of the invention to be positioned and shaped before the material becomes unworkable. Suitable working times are aptly 1 to 6 minutes more aptly 2 minutes to 4 minutes. The curing reaction of the resin system should, however, be sufficiently fast to permit the formed cast or splint to become supportive and load-bearing as soon as possible after completion of working. Aptly the material will set and become supportive between 5 and 30 minutes, more aptly within 15 minutes and particularly in the case of a splint, will aptly become load-bearing within 60 minutes, more aptly after 10 minutes.

The splint may be readily removed by conventional means such as by cutting with a convention vibrating sawtooth disc.

The orthopaedic splinting material of the invention should be protected during storage from water and moisture vapour to prevent a premature setting taking place. The splinting material can be conventionally packaged in heat sealed pouches such as metal foil polyethylene laminate pouches.

The present invention will now be described without limitation thereof with reference to the accompanying examples. It should be understood that normal precautions for excluding moisture during the chemical reactions were employed.

PolyHEMA Coated Potassium Carbonate

Preparation of polyHEMA coated potassium carbonate was carried out by charging a 3L resin flask with 2-hydroxyethylmethacrylate (250 g), potassium carbonate (250 g, 90 μm sieved and milled) and dry ethyl acetate (2.5L). The flask was provided with a stirrer, purged with nitrogen, and stirred for three hours, followed by addition of bis (4-t-butyl cyclohexyl) peroxydicarbonate (BCHPC, 2% by weight) and stirring for 5½ hours at 55° C.

At the end of the reaction bulking was evident. The material was collected by vacuum filtration and washed with ethyl acetate. The material was then dried for two days in a vacuum oven.

The percentage yield was 96%.

Preparation of Aliphatic Isocyanate Functionalised resins

The materials and amounts used in Examples 1 to 5 are shown in Table 1 below.

TABLE 1

| Materials (g) | Example 1 | Example 2 | Example 3 | Example 4 | Example 5 |
|---|---|---|---|---|---|
| PEG 3350 | 1.42 | 5.67 | 5.64 | 2.80 | 0.9 |
| PEG 1500 | 3.82 | 15.22 | 15.15 | 7.52 | 5.37 |
| PEG-5E0 | 1.84 | 7.31 | 7.27 | 3.61 | — |
| Methy-N-Piperazine | — | 2.50 | 4.98 | 5.01 | 3.75 |
| Piperidine | 2.17 | 6.51 | 4.39 | — | — |
| EP2001 | 5.02 | 19.98 | 19.88 | 9.87 | 3.25 |
| DN3400 | 11.49 | 45.92 | 45.88 | 22.89 | 11.80 |
| HDT-LV | 24.24 | 96.90 | 96.82 | 48.30 | 24.19 |
| Metatin 812ES | 0.1 | 0.04 | 0.4 | 0.2 | 0.1 |
| % of bound-in catalyst w/w | 0.0% | 1.25% | 2.5% | 5.0% | 7.5% |

The following procedure illustrates the preparation of water curable resin compositions as formulated in Examples 1 to 5 in Table 1.

Method for Preparing Resins. Examples 1 to 5

The polyols (PEG 3350, PEG 1500, BPA 5EO, EP 2001) were weighed into a predried flask, heated to 60° C. and stirred to give a homogeneous mixture. Approximately 70% of this mixture was decanted into a predried flask, provided with a stirrer, an inlet port and flushed with nitrogen. To this was added the first isocyanate (DN3400) and the metatin before stirring for one hour at 90° C. Subsequently the second isocyanate Tolonate™ HDT-LV was added under nitrogen while stirring.

The tertiary amine (methyl-N-piperazine) was diluted by mixing with the remaining 30% of the polyol and then added to the isocyanate mixture. Stirring continued for a further hour at 90° C., before cooling the mixture.

Preparation of Resin Systems Prepared in Examples 1–4 Containing Potassium Carbonate PolyHEMA coated potassium carbonate was prepared as herein before described to give a solid catalyst comprising 50% potassium carbonate and 50% polyHEMA.

Coated potassium carbonate (2.5%, 5% and 7.5% w/w) was stirred into the resins prepared in Examples 1–4 and the curable compositions were sealed in an airtight container.

Preparation of Orthopaedic Splinting Materials

The resin formulations obtained in Examples 1 to 5, with and without coated potassium carbonate were coated onto dry glass fibre substrates by passing the substrate through the resin system followed by passing the coated substrate through a nip roller, adjusted to a suitable pressure for obtaining a coating weight of 50–60% w/w coating. The coated substrate was then dipped in water, squeezed several times to allow water to impregnate throughout the substrate, and used to bandage around the forearm of an artificial limb (which approximated the contours of a human forearm).

It was found that a hard, smooth cast was formed within 4–100 minutes (Table 2) when the wet, impregnated substrate was applied. The resin has a viscosity which allowed the splinting material to be easily worked so that a smooth cast could be formed.

The effect on cure time of adding a bound-in catalyst and a solid inorganic catalyst in various amounts is illustrated in Table 2 and summarised in Table 3 below.

TABLE 2

| Bound-in tertiary amine catalyst % w/w | Average Curing Time (minutes) POTASSIUM CARBONATE# % w/w | | | |
|---|---|---|---|---|
| | 0% | 1.25% | 2.5% | 3.75% * |
| Example 1 0% | 60+ | — | 13.5 | 12.0 |
| Example 2 1.25% | 26 | 7 | — | — |
| Example 3 2.5% | 12.5 | — | 4.5 | — |
| Example 4 5.0% | 11.3 | — | 5.0 | — |
| Example 5 7.5% | 7.5 | — | — | — |

Potassium carbonate ($K_2CO_3$) was added as $K_2CO_3$ coated with Poly-HEMA (1:1). [PolyHEMA added without $K_2CO_3$ had no effect on the reaction rates.]
* it was practically not feasible to add more than 3.75% w/w $K_2CO_3$ (7.5% w/w coated $K_2CO_3$).

TABLE 3

| Total catalyst level | Catalyst | Cure time (mins) |
|---|---|---|
| 2.5% w/w | 2.5% bound-in tertiary amine catalyst | 12.5 |
| | 2.5% $K_2CO_3$ | 13.5 |
| | 1.25% $K_2CO_3$ and 1.25% bound-in amine catalyst | 7 |
| 5.0% w/w | 5.0% bound-in tertiary amine catalyst | 11.3 |
| | 2.5% $K_2CO_3$ and 2.5% bound-in tertiary amine catalyst | 4.5 |
| 7.5% w/w | 7.5% bound-in tertiary amine catalyst | 7.5 |
| | 2.5% $K_2CO_3$ and 5.0% bound-in tertiary amine catalyst | 5.0 |

TABLE 4

Materials Used in Examples 1–5

| Description/Supplier | Components |
|---|---|
| PEG 3350 | Polyethylene Glycol (Mwt 3350) |
| BPA 5EO | Ethoxylated Bis-phenol A |
| Jeffamine ™ EDR-148 (obtainable from Huntsman Corp.) | Diamine Chain Extender |
| Methyl-n-piperazine (obtainable from Aldrich Chemical Co UK Ltd) | Bound-in Catalyst |
| Desmodur ™ N3400 (obtainable from Whitfield Chemicals) | Aliphatic isocyanate HDI based (hexamethylene diisocyanate) |
| Anitfoam MSA (obtainable from Ellis-Everard Inc USA) | Silicone based Antifoaming agent |
| Metatin 813ES | Tin Catalyst |
| Coated $K_2CO_3$ | 50/50 PolyHEMA Coated Potassium Carbonate |
| PEG 1500 | Polyethylene Glycol (Mwt 1500) |
| Voranol ™ EP2001 (obtainable from K & K Greeff Ltd. UK) | Ethyleneoxide end-capped Polypropylene Glycol |
| Tolonate ™ HDT-LV (obtainable from Rhone Poulenc) | Aliphatic Isocyanate (HDI Trimer) |

What is claimed is:

1. A resin system comprising at least a water curable, isocyanate functionalised prepolymer and a first and a second catalyst component wherein the first catalyst comprises a tertiary amine catalyst chemically bound-in to the prepolymer, the bound-in tertiary amine catalyst being selected from the group consisting of:

1-(2-hydroxyethyl) pyrrolidine, 1-methyl piperazine, 1-methyl-2-piperidine methanol, 1,4-bis(2-hydroxyethyl) piperazine 2[2-(dimethylamino)ethyl]methyl amino ethanol, gramine, 3-morpholino-1,2-propanediol, 1,4-bis(3-aminopropyl)piperazine, tropine, 3-aminopropyl morpholine, 4,2-hydroxyethyl morpholine, 3,3-diamino-N-methyl dipropylamine, 1,4-bis(2-hydroxypropyl)-2-methyl piperazine, 1-(2-hydroxypropyl)imidazole, 3-dimethyl amino propanol and β-hydroxy-4-morpholine propane sulphonic acid, and the second catalyst is not chemically bound-in and is water soluble but insoluble in the prepolymer.

2. A resin system according to claim 1 wherein the tertiary amine catalyst comprises a single chemical species.

3. A resin system according to claim 1 wherein the first catalyst comprises less than 10% and at least 0.1% by weight of the resin system.

4. A resin system according to claim 1 wherein the second catalyst is a solid inorganic catalyst.

5. A resin system according to claim 1 wherein the second catalyst is coated with a hydrophilic coating.

6. A resin system according to claim 1 wherein the second catalyst comprises less than 10% and at least 0.1% by weight of the resins system.

7. A resin system according to claim 1 wherein the first catalyst and the second catalyst together comprise less than 7.5% by weight of the resin system.

8. A resin system according to claim 1 wherein the first catalyst and the second catalyst each comprise 2.5% by weight of the resin system.

9. A resin system according to claim 1 wherein the isocyanate functionalised prepolymer is an aliphatic isocyanate functionalised prepolymer.

10. An orthopaedic splinting material comprising a flexible substrate carrying a resin system according to claim 1.

11. An orthopaedic splinting material according to claim 10 wherein said resin system further includes additives selected from the group consisting of fillers, pigments, fragrances, surfactants, lubricants or mixtures thereof.

12. An orthopaedic splinting material according to claim 10 wherein the resin system is coated onto the flexible substrate.

13. An orthopaedic splinting material according to claim 10 wherein the resin system comprises 30 to 80% by weight of the splinting material.

14. A method for treating a fracture of a body part comprising wetting the splinting material according to claim 10 applying and shaping the splinting material around the body part and allowing the splinting material to set by curing of the prepolymer.

15. A resin system comprising at least a water curable, isocyanate functionalised prepolymer and a first and a second catalyst component wherein the first catalyst is chemically bound-in to the prepolymer and the second catalyst is not chemically bound-in, is coated with a hydrophilic coating, and is water soluble but insoluble in the prepolymer.

16. A resin system according to claim 15 wherein the first catalyst is covalently bound-in to the prepolymer.

17. A resin system according to claim 15 wherein the first catalyst comprises a tertiary amine catalyst.

18. A resin system according to claim 17 wherein the tertiary amine catalyst comprises a single chemical species.

19. A resin system according to claim 17 wherein the first catalyst comprises less than 10% and at least 0.1% by weight of the resin system.

20. A resin system according to claim 17 wherein the bound-in tertiary amine catalyst is selected from the group consisting of:
   1-(2-hydroxyethyl) pyrrolidine, 1-methyl piperazine,
   1-methyl-2-piperidine methanol, 1,4-bis(2-hydroxyethyl) piperazine
   2[2-(dimethylamino)ethyl]methyl amino ethanol, gramine, 3-morpholino-1,2-propanediol, 1,4-bis(3-aminopropyl)piperazine, tropine,
   3-aminopropyl morpholine, 4,2-hydroxyethyl morpholine,
   3,3-diamino-N-methyl dipropylamine,
   1,4-bis(2-hydroxypropyl)-2-methyl piperazine,
   1-(2-hydroxypropyl)imidazole, 3-dimethyl amino propanol and β-hydroxy-4-morpholine propane sulphonic acid.

21. A resin system according to claim 15 wherein the second catalyst is a solid inorganic catalyst.

22. A resin system according to claim 15 wherein the second catalyst comprises less than 10% and at least 0.1% by weight of the resins system.

23. A resin system according to claim 15 wherein the first catalyst and the second catalyst together comprise less than 7.5% by weight of the resin system.

24. A resin system according to claim 15 wherein the first catalyst and the second catalyst each comprise 2.5% by weight of the resin system.

25. A resin system according to claim 15 wherein the isocyanate functionalised prepolymer is an aliphatic isocyanate functionalised prepolymer.

26. An orthopaedic splinting material comprising a flexible substrate carrying a resin system according to claim 15.

27. An orthopaedic splinting material according to claim 26 wherein said resin system further includes additives selected from the group consisting of fillers, pigments, fragrances, surfactants, lubricants or mixtures thereof.

28. An orthopaedic splinting material according to claim 26 wherein the resin system is coated onto the flexible substrate.

29. An orthopaedic splinting material according to claim 26 wherein the resin system comprises 30 to 80% by weight of the splinting material.

30. A method for treating a fracture of a body part which comprises wetting the splinting material according to claim 26 applying and shaping the splinting material around the body part and allowing the splinting material to set by curing of the prepolymer.

31. An orthopaedic splinting material comprising at least a water curable, isocyanate functionalised prepolymer and a first and a second catalyst component wherein the first catalyst comprises a tertiary amine catalyst chemically bound-in to the prepolymer, the bound-in tertiary amine catalyst being selected from the group consisting of:
   1-(2-hydroxyethyl) pyrrolidine, 1-methyl piperazine,
   1-methyl-2-piperidine methanol, 1,4-bis(2-hydroxyethyl) piperazine
   2[2-(dimethylamino)ethyl]methyl amino ethanol,
   gramine, 3-morpholino-1,2-propanediol,
   1,4-bis(3-aminopropyl)piperazine, tropine,
   3-aminopropyl morpholine, 4,2-hydroxyethyl morpholine,
   3,3-diamino-N-methyl dipropylamine,
   1,4-bis(2-hydroxypropyl)-2-methyl piperazine,
   1-(2-hydroxypropyl)imidazole, 3-dimethyl amino propanol and β-hydroxy-4-morpholine propane sulphonic acid, and the second catalyst is not chemically bound-in and is water soluble but insoluble in the prepolymer.

32. An orthopaedic splinting material comprising at least a water curable, isocyanate functionalised prepolymer and a first and a second catalyst component wherein the first catalyst is chemically bound-in to the prepolymer and the second catalyst is not chemically bound-in, is coated with a hydrophilic coating, and is water soluble but insoluble in the prepolymer.

33. A resin system comprising at least a water curable, isocyanate functionalized prepolymer and formed by a curing reaction catalyzed by:
   (a) a first chemically in-bound catalyst comprising a tertiary amine catalyst selected from the group consisting of 1-(2-hydroxyethyl) pyrrolidine, 1-methyl piperazine, 1-methyl-2-piperidine methanol, 1,4-bis(2-hydroxyethyl) piperazine 2[2-(dimethylamino)ethyl] methyl amino ethanol, gramine, 3-morpholino-1,2-propanediol, 1,4-bis(3-aminopropyl)piperazine, tropine, 3-aminopropyl morpholine, 4,2-hydroxyethyl morpholine, 3,3-diamino-N-methyl dipropylamine, 1,4-bis(2-hydroxypropyl)-2-methyl piperazine, 1-(2-hydroxypropyl)imidazole, 3-dimethyl amino propanol, and β-hydroxy-4-morpholine propane sulphonic acid; and
   (b) a second chemically not bound-in catalyst soluble in water and insoluble in said prepolymer;
      wherein said first and second catalysts together show a synergistic effect whereby the reaction rate between water and the prepolymer is increased.

34. A resin system comprising at least a water curable, isocyanate functionalized prepolymer and formed by a curing reaction catalyzed by a first chemically bound-in catalyst and a second not chemically bound-in catalyst coated with a hydrophilic coating, soluble in water and insoluble in said prepolymer, wherein said first and second catalysts together show a synergistic effect whereby the reaction rate between water and the prepolymer is increased.

* * * * *